(12) United States Patent
Quint et al.

(10) Patent No.: US 11,771,874 B2
(45) Date of Patent: Oct. 3, 2023

(54) FUNCTIONALIZED BALLOON SURFACE

(71) Applicant: BIOTRONIK AG, Bülach (CH)

(72) Inventors: Bodo Quint, Dettighofen (DE); Jeremy Wernli, Wettingen (CH)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 17/619,660

(22) PCT Filed: Jun. 23, 2020

(86) PCT No.: PCT/EP2020/067463
§ 371 (c)(1),
(2) Date: Dec. 16, 2021

(87) PCT Pub. No.: WO2021/001209
PCT Pub. Date: Jan. 7, 2021

(65) Prior Publication Data
US 2022/0305240 A1 Sep. 29, 2022

(30) Foreign Application Priority Data
Jul. 2, 2019 (EP) .................... 19183858

(51) Int. Cl.
*A61M 25/10* (2013.01)
*D01D 5/00* (2006.01)

(52) U.S. Cl.
CPC ......... *A61M 25/1029* (2013.01); *D01D 5/003* (2013.01); *A61M 2025/105* (2013.01); *A61M 2025/1031* (2013.01); *A61M 2025/1075* (2013.01); *D10B 2509/00* (2013.01)

(58) Field of Classification Search
CPC ............................................... A61M 25/1029
See application file for complete search history.

(56) References Cited

U.S. PATENT DOCUMENTS

| 9,744,316 B2* | 8/2017 | Vogt | A61M 3/0279 |
| 2004/0211337 A1* | 10/2004 | Lee | C09K 3/1409 |
| | | | 438/692 |
| 2006/0184112 A1* | 8/2006 | Horn | A61L 29/126 |
| | | | 604/103.08 |
| 2007/0232996 A1* | 10/2007 | Andersen | A61M 25/104 |
| | | | 604/103.02 |
| 2008/0157444 A1* | 7/2008 | Melsheimer | D01D 5/0076 |
| | | | 264/514 |

(Continued)

FOREIGN PATENT DOCUMENTS

| CN | 103998115 A * | 8/2014 | ........... B01D 61/364 |
| EP | 2248541 A2 * | 11/2010 | ............. A61L 2/085 |

(Continued)

OTHER PUBLICATIONS

International Search Report and Written Opinion from the corresponding International Patent Application No. PCT/EP2020/067463, dated Sep. 11, 2020.

*Primary Examiner* — Cachet I Proctor
(74) *Attorney, Agent, or Firm* — Greer, Burns & Crain, Ltd.; Steven P. Fallon

(57) ABSTRACT

A method for producing a balloon for a balloon catheter includes providing the balloon that has an outer surface. A solution including a solvent and a polymer is used to deposit the polymer onto the surface and form a surface coating of the polymer.

12 Claims, 4 Drawing Sheets

(56) References Cited

U.S. PATENT DOCUMENTS

| | | | | |
|---|---|---|---|---|
| 2008/0183132 | A1* | 7/2008 | Davies | A61M 25/104 |
| | | | | 604/103.09 |
| 2010/0286608 | A1 | 11/2010 | Tittelbach et al. | |
| 2013/0268062 | A1* | 10/2013 | Puckett | D04H 1/728 |
| | | | | 156/190 |
| 2014/0276404 | A1* | 9/2014 | Orlowski | A61L 29/16 |
| | | | | 604/103.02 |
| 2017/0119886 | A1* | 5/2017 | Johnson | A61L 27/54 |
| 2018/0179680 | A1* | 6/2018 | Gruba | A61L 27/3895 |
| 2019/0053897 | A1* | 2/2019 | Levi | A61F 2/2418 |

FOREIGN PATENT DOCUMENTS

| | | | | |
|---|---|---|---|---|
| JP | 2003225301 A | 8/2003 | | |
| KR | 20180012885 A | 2/2018 | | |
| WO | WO-2005065578 A2 * | 7/2005 | ............. | A61B 17/11 |
| WO | WO-2005105171 A1 * | 11/2005 | ............. | A61F 2/958 |
| WO | WO-2008037028 A1 * | 4/2008 | ............. | A61K 38/39 |
| WO | 2014125465 A2 | 8/2014 | | |

\* cited by examiner

FUNCTIONALIZED BALLOON SURFACE

PRIORITY CLAIM

This application is a 35 U.S.C. 371 US National Phase and claims priority under 35 U.S.C. § 119, U.S.C. 365(b) and all applicable statutes and treaties from prior PCT Application PCT/EP2020/067463, which was filed Jun. 23, 2020, which application claimed priority from European Application Serial Number 19183858.0, which was filed Jul. 2, 2019.

FIELD OF THE INVENTION

A field of the invention includes balloons used in balloon catheter systems, such as balloon catheter systems used to implant stents.

BACKGROUND

Surfaces of balloons used, for example, in balloon catheter systems, for example for implanting stents, are particularly important since an appropriate modification allows the stent retention force on the balloon to be increased, for example, or the properties of the balloon surface as a carrier for additional components, such as electrical lines or drug coatings to be improved.

Known drug-coated balloons often include relatively thick coagulate coatings. However, membranes of balloons are often too finely structured and, as a result, are not able to sufficiently adhere such existing coating formulations.

During the stent expansion, intensive shearing forces arise in stent delivery systems, wherein as the adhesion of the coating to the balloon itself, or the strength of the coating, are often limiting. There is a risk due to abrasion of the coating or the delamination thereof (particle emissions).

Moreover, printing inks and electrically printable conductive tracks regularly use mild, and preferably safe, solvent systems, which are less suitable for polymer systems and can themselves be very easily dissolved by common solvents, such as alcohols or acetone. For this reason, some of these technical systems are additionally refined with a chemical curing mechanism, which, in general, is triggered thermally. However, since conventional printed circuit board materials are considerably more stable thermally than balloon surfaces, the process conditions required here are difficult to implement. With insufficient thermal fixation, these printed structures are quickly partially dissolved by subsequent application layers.

SUMMARY OF THE INVENTION

A preferred method for producing a balloon for a balloon catheter creates a balloon surface that provides increased friction, or improved adhesion promotion to subsequent coatings or a crimped stent, or protection for an additional component of the balloon.

A preferred method includes providing a balloon. The balloon has an outer surface. A solution is provided including a solvent and a polymer dissolved therein. The polymer is deposited onto the surface for and forms a surface coating of the polymer, on the surface of the balloon.

BRIEF DESCRIPTION OF THE DRAWINGS

Embodiments and further features and advantages of the invention will be described hereafter based on the figures. In the drawings.

DETAILED DESCRIPTION OF THE PREFERRED EMBODIMENTS

Figure 1:
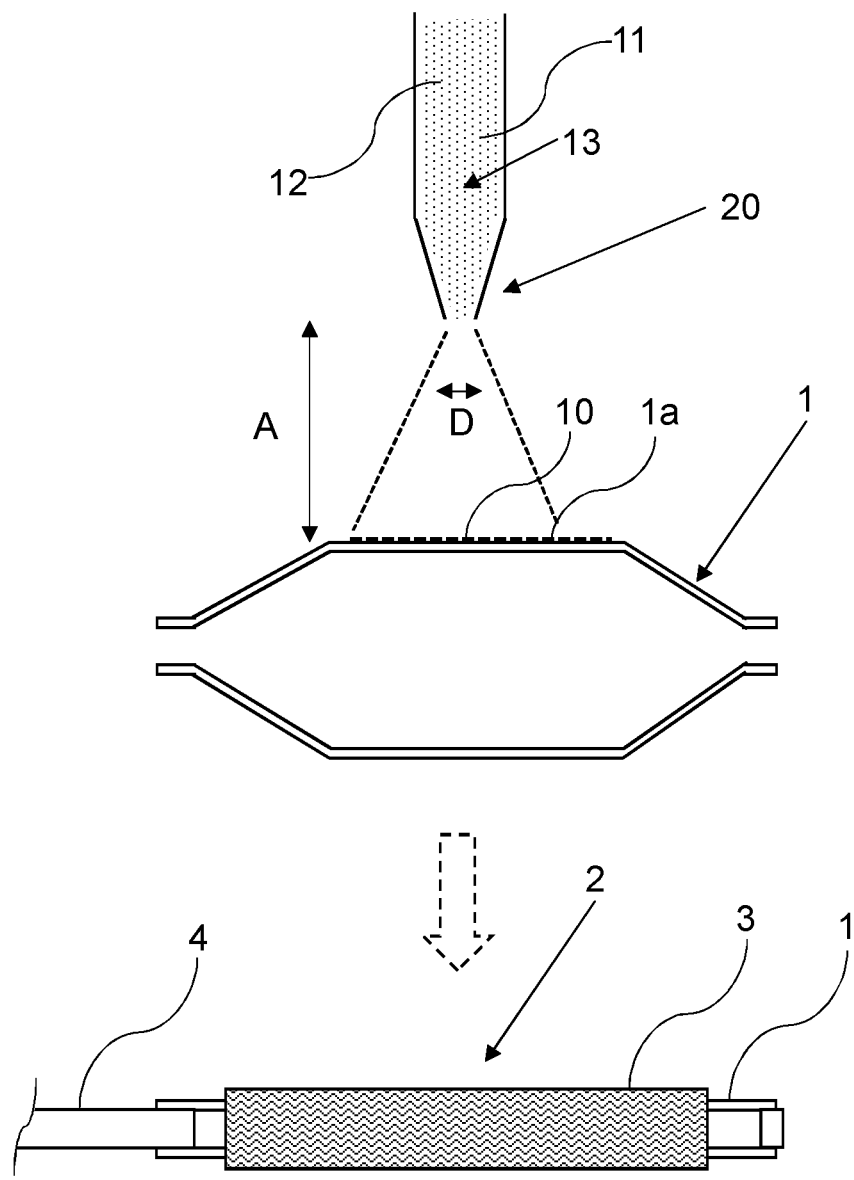
FIG. 1 shows a schematic illustration of one embodiment of the method according to the invention.

The method according to the invention allows a surface coating to be produced, which has a roughened surface composed, for example, of a polymer-analogous material of the balloon material. This material is, in particular, inherently joined to a base material of the balloon by way of a swelling/partial solution process. The created surface coating, in general, includes a "nonwoven-like" structuring since predominantly fiber-like particle structures are created, even under spray conditions due to the spraying action and minimal surface tension of the solvent used. In particular, it is possible to achieve coating wall thicknesses of less than 5 micrometers.

According to one embodiment of the method, the solvent is one of the following acids: trifluoroacetic acid ($C_2HF_3O_2$, CAS number 76-05-1).

According to one embodiment of the method, it is further provided that the polymer (11) is one of the following polymers: an aliphatic or aromatic polyamide, or a thermoplastic polymer such as a polyether block amid copolymer, for example PEBAX 6233.

According to one embodiment of the method, it is further provided that the polymer, in the solution, has a concentration in the range of 1 wt. % to 30 wt. %, and preferably 1 to 10 wt. %. In one embodiment, it is preferred when the polymer, in the solution, has a concentration in the range of 15 to 25 wt. %. In particular, an electrospinning process can advantageously be carried out in such a range. In another embodiment, it is preferred when the polymer, in the solution, has a concentration in the range of 1 to 20 wt. %. The electrospinning process can be carried out particularly advantageously in such an embodiment.

According to one embodiment of the method, it is further provided that, for the deposition of the polymer on the surface of the balloon, the solution is sprayed by way of a nozzle in a direction toward the surface, wherein, in particular, fibrous structures of the polymer are formed. This can be achieved, for example, by an airbrush method or an electrospinning process.

According to one embodiment of the method, it is further provided that the nozzle has an inside diameter in the range of 0.1 mm to 1.2 mm.

According to one embodiment of the method, it is further provided that the nozzle has a distance from the surface of the balloon of greater than or equal to 10 cm during spraying of the solution.

According to a further preferred embodiment of the method, it is provided that polymer of the solution is deposited or applied onto the surface of the balloon in fibrous form.

According to one embodiment of the method, it is further provided that the balloon includes one of the following substances or is formed of one of the following substances: an aliphatic or aromatic polyamide or a thermoplastic elastomer-modified polymer, such as a polyether block amide (PEBA).

According to one embodiment of the method, it is further provided that the surface coating is coated with a drug or a composition containing a drug.

According to one embodiment of the method, it is further provided that the balloon includes at least one electrical conductor on the surface of the balloon prior to the deposition of the polymer, and wherein the generated surface coating preferably protrudes beyond a region of the surface coating covering the at least one conductor, in a manner normal to the surface of the balloon in a surrounding area of the at least one conductor. The at least one conductor can be created, for example, by printing the surface of the balloon using an electrically conductive ink.

Another aspect of the present invention relates to a balloon for a balloon catheter, wherein the balloon is produced by way of the method according to the invention.

Another aspect of the present invention relates to a balloon catheter, including a balloon according to the invention and a stent arranged on the surface coating of the balloon.

Another aspect of the present invention relates to a use of a solution, including trifluoroacetic acid, as the solvent, and a polymer dissolved in the solvent for coating an outer surface of a balloon.

The polymer can have the above-described concentration in the solution. The polymer can further be one of the polymers described above in the present connection.

FIG. 1 shows a schematic illustration of one embodiment of a method according to the invention for producing a balloon 1 for a balloon catheter 2, including the following steps:

providing the balloon 1, wherein the balloon 1 has an outer surface 1a;

providing a solution 13, including a solvent 11 and a polymer 12 dissolved therein, wherein Pebax 6233 is dissolved here, for example, as the polymer 12 in trifluoroacetic acid in a concentration of 1 wt. % to 5 wt. %; and depositing the polymer 12 onto the surface 1a for forming a surface coating 10, including the polymer 12, on the surface 1a of the balloon 1.

In this regard, the trifluoroacetic acid advantageously has a very unusual wetting behavior since this compound is based on a very small molecule that is "ultrahydrophobic" at one end and, at the opposite molecule end, represents a "highly polar" organic acid. Due to this structure, it tends to virtually crawl out of glass/porcelain vessels, for example. Despite the acidic effect and the high polarity, this compound forms surfaces having very low surface tension and very good wetting action.

A plurality of polyamides, as well as the PEBA copolymers typical in catheter production, are soluble in trifluoroacetic acid. Spraying surfaces 1a of such balloons with the aforementioned solution 13 leads to surprising results.

For example, at a spraying distance A between the nozzle 20 and the surface 1a of greater than or equal to 10 cm, and an inside diameter D of the nozzle 20 in the range of 0.1 mm to 1.2 mm, as well as a spraying pressure of approximately 3 bar, it was possible to observe gel-like depositions on the surface 1a, which still cause relaxations at the balloon 1, but no longer deform the balloon to any great degree. Despite spraying on one side, straight components without notable deformation were obtained with a support pressure of the balloon made of PA12 of 1 bar. It was surprising, however, that surface depositions that were still rough and have a nonwoven-like structure obtained across a very large dilution range.

Figure 2:
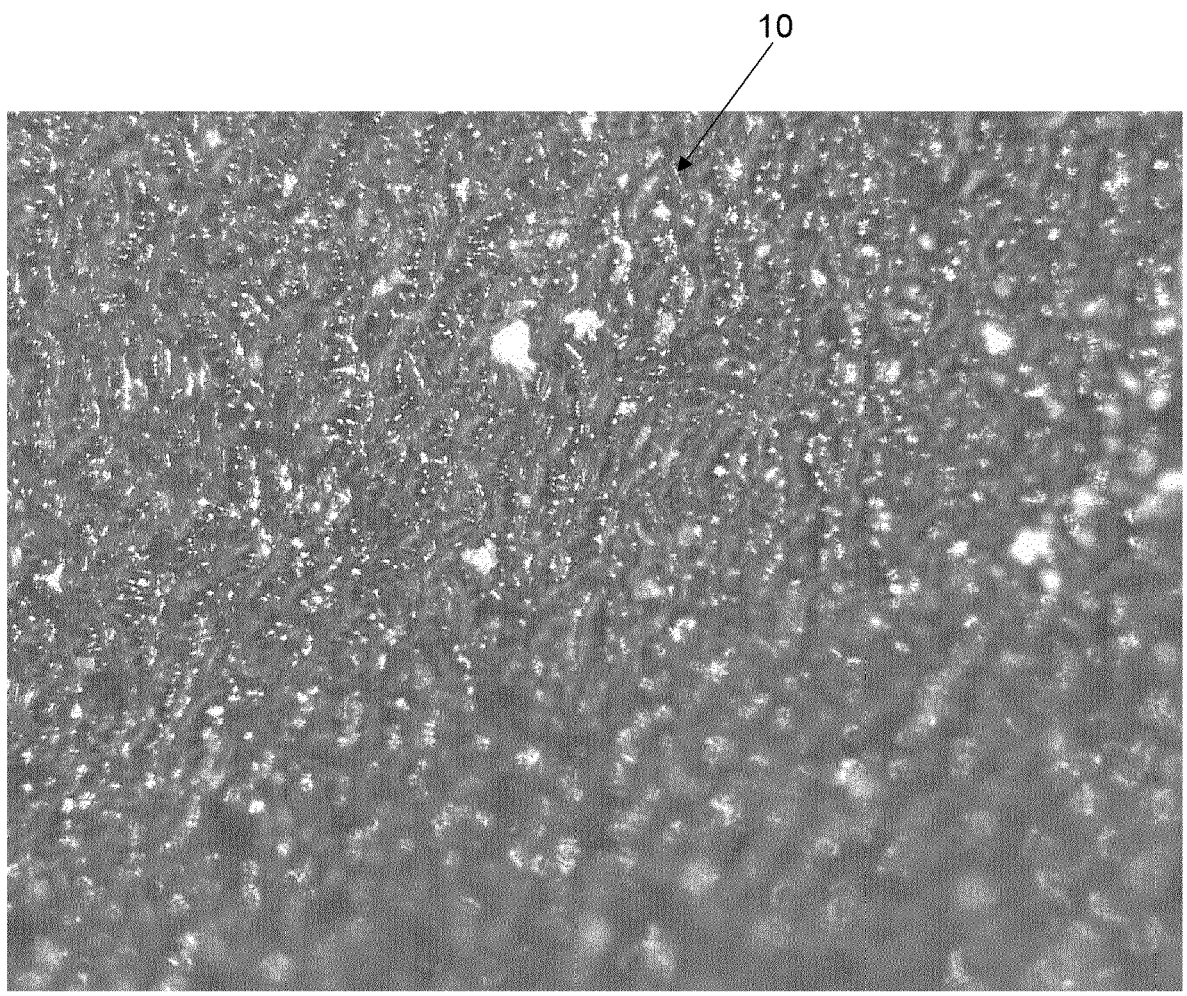
FIG. 2 shows a photographic representation (200× magnification) of a rough, homogeneously distributed surface coating made of a polyether block amide Pebax 6333, which was created by way of the method according to the invention.
Figure 3:
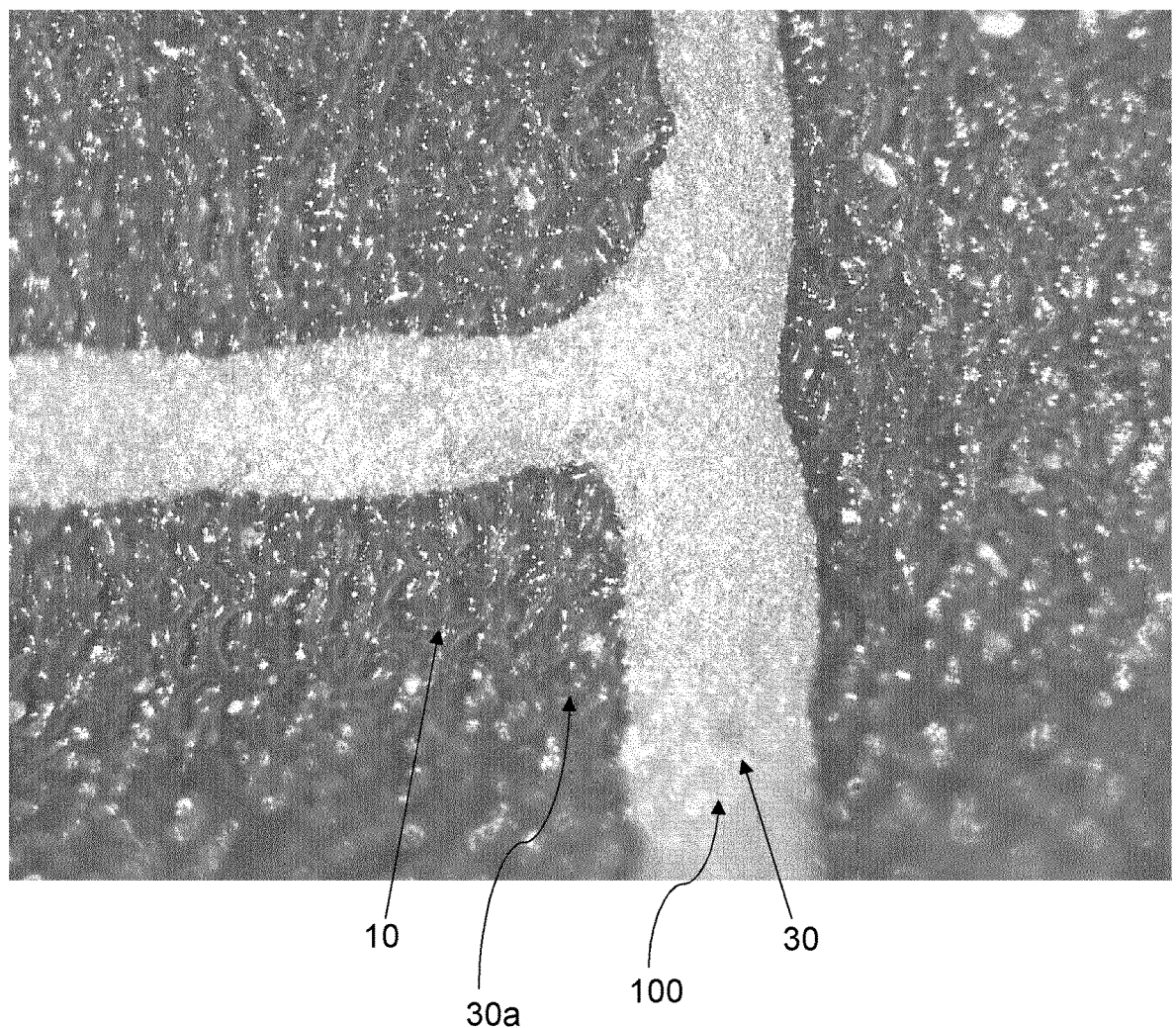
FIG. 3 shows a photographic representation (200× magnification) of a surrounding area of a printed conductor structure on a balloon generated by way of the method according to the invention.
Figure 4:
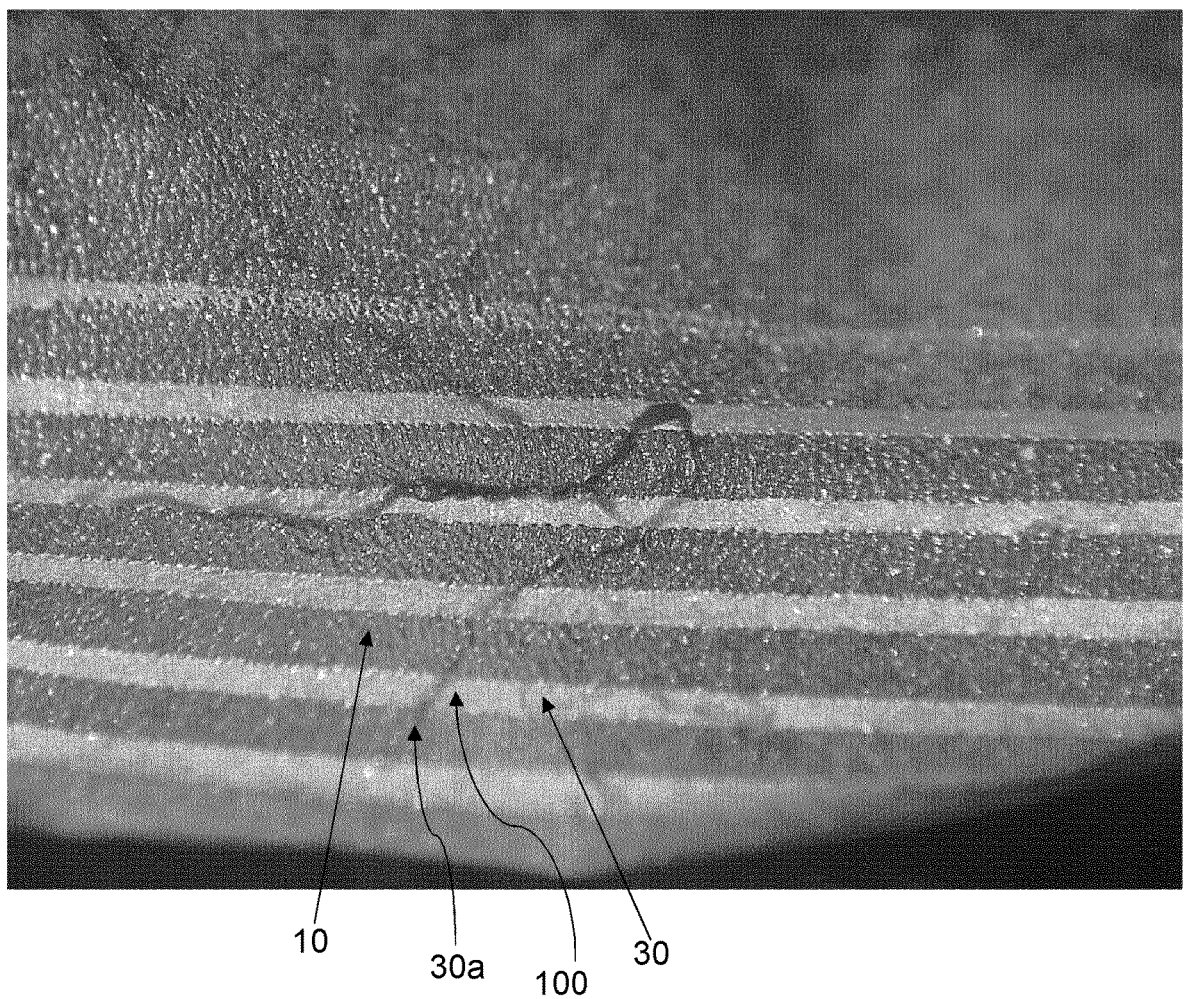
FIG. 4 shows a photographic representation (50× magnification) of a surface coating generated by way of the method according to the invention.

This structure is identified in FIGS. 2 to 4 by dyeing of the coating solution 13 with rhodamine. At >>100-fold magnifications, a complex surface structure that is structured in the micrometer range is apparent (see FIG. 2).

The balloon 1 to be coated can further include a printed conductor structure, for example, such is as in the form of an electrical conductor 30. FIG. 3 shows in this regard that the surface coating on the balloon 1 in the surrounding area of the conductors 30 spontaneously gels as a result of a loss of solvent to the underlying polyamide, while the wetting effect outweighs on the particular conductor 30, resulting in a planar and thin insulating coating 100 on this substrate. The respective conductor 30 is thus mechanically embedded into the newly created surface by way of a high-strength, flexible material, and can thus be protected against peeling or shear load.

According to FIG. 4 (50× magnification), the surrounding spray region located further away also includes spider web-like deposits when the spray coating is implemented using a needle-shaped nozzle arrangement.

Due to the low surface tension of the trifluoroacetic acid and the viscosity of the polymer solutions, the spraying process (and the utilized nozzle geometry) preferably creates thread-shaped fragments, which are preserved in the gas phase due to solvent loss.

As a result of the low surface tension, the polymer 12 is pulled off in a thread-like manner in the pointed nozzle 20, and this structure will be preserved approximately unchanged during the spray phase due to the high vapor pressure. These fibrous particles are deposited on the surface 1a in gel-like form, where they suffer a considerable loss of volume due to the drying process, which is intensified by the suctioning or solvent-withdrawing action of the polyamide balloon surface 1a.

Since trifluoroacetic acid represents an intensive solvent for polyamide 12, this residual moisture creates solvent adhesion to the substrate. This surface cannot be abraded/separated from the surface 1a even with intensive abrasive action.

These properties, the low surface tension and very spontaneous gel formation predestine the solution 13 for an electrospinning or electrospraying process. Since both smaller material transfer volumes and greater control over the deposition can be achieved here, the electrospinning process is one of the preferred methods for applying the surface coating 10.

As is further shown in FIG. 1, the created surface structure is, in particular, also suitable for increasing the achievable stent retention force or for increasing adhesion of a drug coating.

In other steps of the method, the balloon 1 can be accordingly completed to form a catheter 2. The catheter 2 receives a shaft 4 in the process, wherein the balloon 1 is fixed at the distal end of the shaft 4, and wherein a stent 3 can be crimped onto the folded balloon 1 or onto the surface coating 10. Instead of a stent 3, the surface coating 10 of the balloon 1 can be provided with a drug coating.

The surface coatings 10 that can be produced according to the invention advantageously make it possible to introduce an applied active ingredient layer into the newly created surface structure, and thus allow large amounts of an active ingredient to be applied into the irregularities of the balloon coating, The gain in friction with respect to the stent surface can contribute to an improved stent retention force in the case of balloon catheters 2.

The electrical insulation effect is ultimately limited by the surface roughness and structure of the created coating, but it is nonetheless apparent (see FIGS. 3 and 4) that thin coatings that are continuous across a surface area can be achieved after deposition. It is further advantageous that the solvent system 13 does not interact with the typical acrylate-based binders, whereby it is made possible to apply commercially available electrically conducting inks onto the particular balloon surface, without intensive thermal curing and disadvantageous delamination effects. One special feature in the process is the achievable mechanical protection of these printed structures 30 since the surrounding surface coating 10 gains in thickness more quickly than on the printed structures 30 themselves.

As a result of the roughly structured composition 10 adjoining the conductive tracks 30, an increased thickness compared to the particular conductive track 30 is achieved. This means that originally raised conducting electrical structures 30 are present in a mechanically protected and embedded manner after the coating has been carried out.

The invention claimed is:

1. A method for producing a balloon for a balloon catheter, comprising the following steps:
   providing the balloon, wherein the balloon has an outer surface;
   providing a solution comprising a solvent and a polymer dissolved in the solution; and
   depositing the polymer onto the surface from the solution to form a surface coating of the polymer on the surface of the balloon, wherein the solvent and polymer are selected such that fibrous particles are deposited on the surface in gel-like form, and the particles undergo a loss of volume due to the drying after application and due to suctioning or solvent-withdrawing action of the balloon surface.

2. The method according to claim 1, wherein the solvent is trifluoroacetic acid.

3. The method according to claim 2, wherein the polymer is selected from the group consisting of: an aliphatic or aromatic polyamide and a thermoplastic polymer.

4. The method according to claim 3, wherein the polymer in the solution has a concentration in the range of 1 wt. % to 30 wt. %.

5. The method according to claim 3, wherein the polymer is a thermoplastic elastomer-modified polymer.

6. The method according to claim 3, wherein the polymer is a polyether block amide.

7. The method according to claim 1, wherein the polymer of the solution is deposited onto the surface by electrospinning.

8. The method according to claim 1, wherein the balloon comprises one of an aliphatic or aromatic polyamide or a thermoplastic elastomer-modified polymer.

9. The method according to claim 1, further comprising adding a drug or a composition containing a drug on the surface coating.

10. The method according to claim 1, wherein the balloon comprises at least one electrical conductor on the surface of the balloon prior to the deposition of the polymer, the generated surface coating embeds the at least one conductor.

11. The method according to claim 1, wherein the depositing comprises spraying through a shaped nozzle and wherein the solvent and polymer are selected such that the viscosity of the solution creates thread-shaped fragments in a spray from the nozzle that are preserved in the gas phase due to solvent loss.

12. The method according to claim 11, wherein the solution emerges in a thread-like manner from the nozzle.

* * * * *